United States Patent [19]

Meltzer

[11] 4,181,434

[45] Jan. 1, 1980

[54] COLOR COMPENSATION SYSTEM FOR ABBE REFRACTOMETER

[75] Inventor: Robert J. Meltzer, Williamsville, N.Y.

[73] Assignee: American Optical Corporation, Southbridge, Mass.

[21] Appl. No.: 802,741

[22] Filed: Jun. 2, 1977

[51] Int. Cl.² ............................................. G01N 21/46
[52] U.S. Cl. .................................................. 356/137
[58] Field of Search ................. 356/133, 135, 136, 137

[56] References Cited

U.S. PATENT DOCUMENTS 3,267,795 8/1966 Goldberg ............................. 356/137

Primary Examiner—Conrad J. Clark
Attorney, Agent, or Firm—Jeremiah J. Duggan; Alan H. Spencer; Stephen A. Schneeberger

[57] ABSTRACT

The effect of angular errors or mismatching indices of refraction of color-compensation prisms of Abbe refractometers can be virtually eliminated by decentration of the lens used to image light on the refractometer reticle.

4 Claims, 2 Drawing Figures

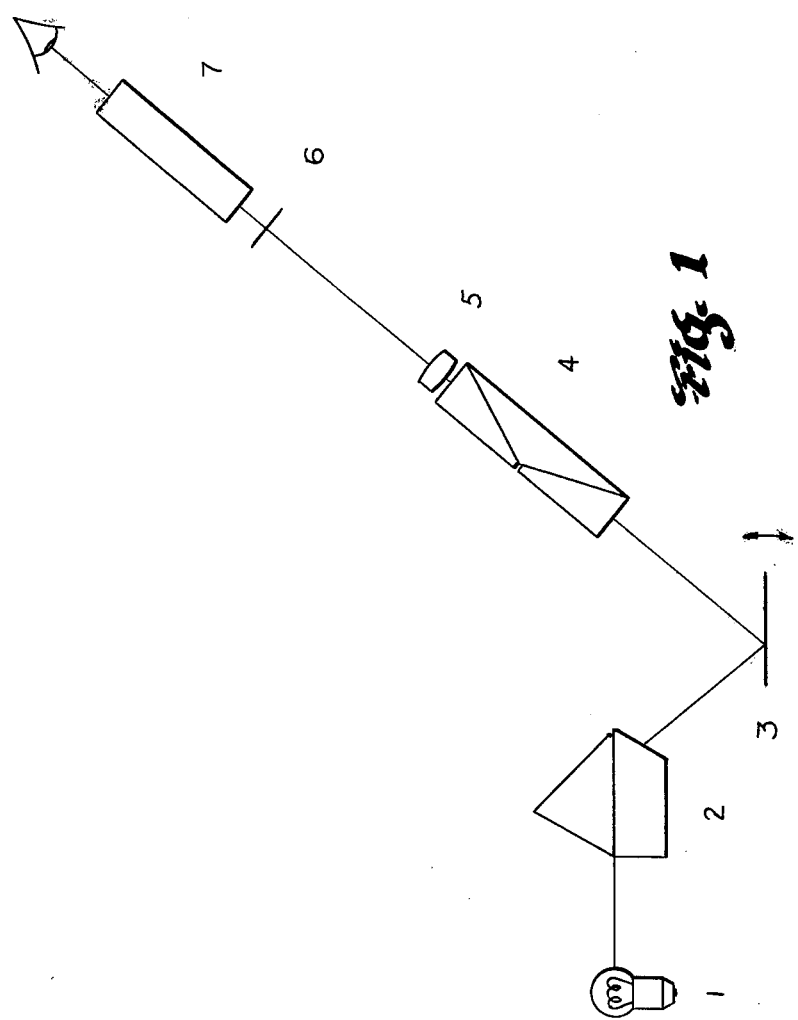

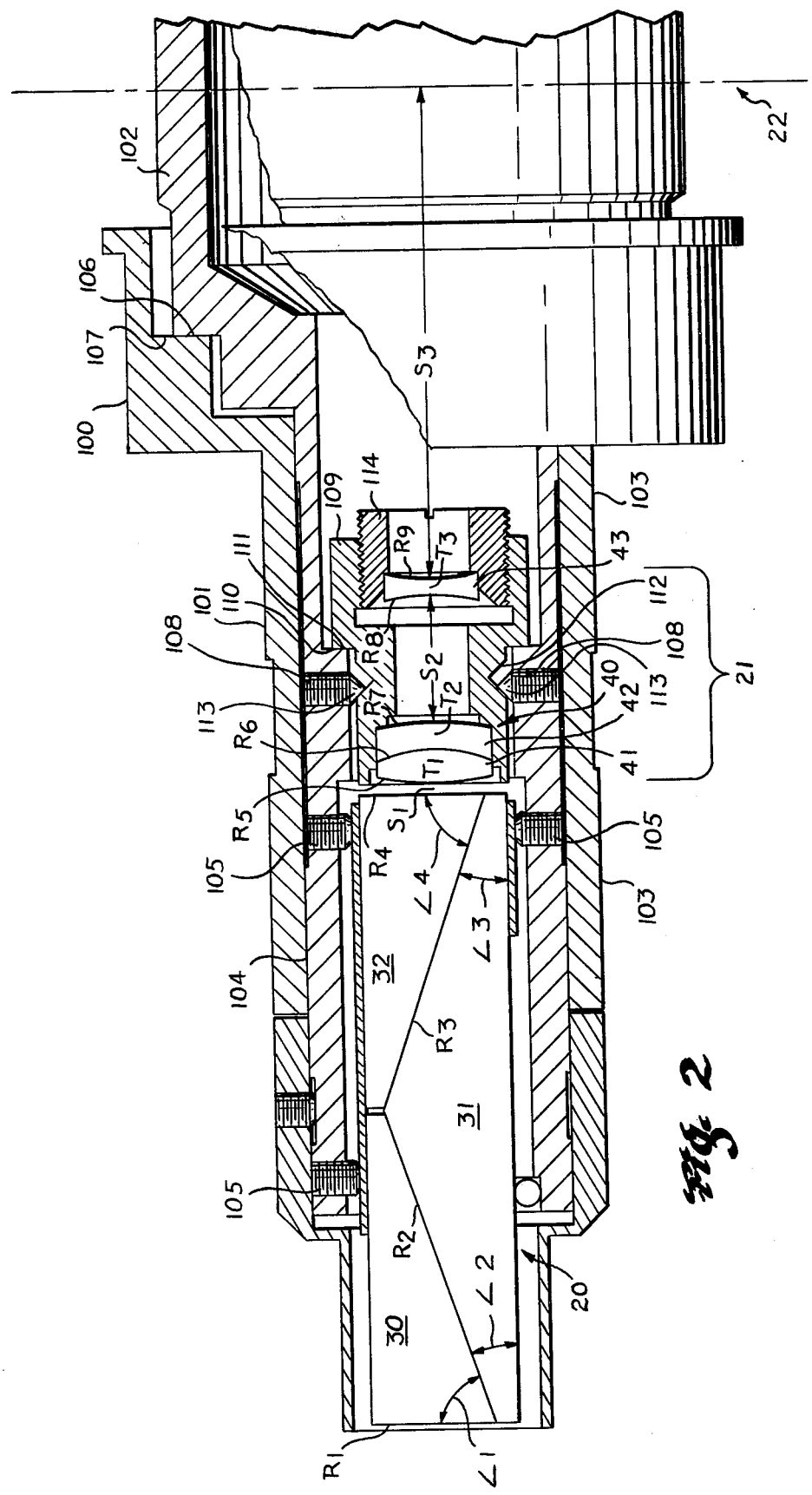

COLOR COMPENSATION SYSTEM FOR ABBE REFRACTOMETER

BACKGROUND OF THE INVENTION

This invention relates to color compensators for Abbe refractometers and more particularly to overcoming inherent problems with color-compensating prisms.

Abbe refractometers are sophisticated refractometers for measuring the index of refraction to determine solution concentration or for material identification. Abbe refractometers generally include some color-compensation means to correct for dispersion occurring in the primary prism when conventional (white) light is used for illumination. It is well known that the different wavelengths of white light are deviated different amounts by a prism. Color-compensation prisms have traditionally been used to recombine the various wavelengths of the light into a full spectrum prior to focusing on the reticle in order to provide a color-free sharp image. In order to avoid full spectrum deviation by the color-compensating prism, it is essential that all angles be precisely equal and opposite and that all indices of refraction be precisely identical. Mismatching of indices of refraction and/or imprecision in the manufacture of equal and opposite angles results in a deviation of the reference light which varies as the color-compensation prism is rotated. Rotation of the color-compensation prism is the conventional manner of adjustment for desired color compensation, since rotation permits the differing dispersion values of the compensating prism materials to be utilized more or less fully to offset the dispersion caused by the primary prism. Generally, such compensating prisms are manufactured to extremely precise specifications in order to avoid more than 10 second deviation of the full spectrum upon rotation of the compensating prism.

STATEMENT OF THE PRIOR ART

One procedure which has been used to avoid deviation is to have a matched pair of compensating prisms which are rotated in opposite directions. An example of such a system is an Abbe refractometer sold by the Assignee for many years having the optical system shown in the attachment hereto. This solution, however, required complicated and expensive support mechanisms having little tolerance for misalignment or decentration of either member of the pair and precise control of prism movement.

Compensating prisms in refractometers are also taught by U.S. Pat. Nos. 2,966,091 issued Dec. 27, 1960 to H. E. Goldberg and 2,972,962 issued Feb. 28, 1961 to E. Goldberg et al. Neither of these patents, nor any other prior art of which the inventor or his attorney is aware provides for correction of deviation errors caused by the color-compensating prism by means of decentration of a lens.

BRIEF DESCRIPTION OF THE PRESENT INVENTION AND DRAWINGS

The deviation resulting from unequal angles and/or mismatched indices of refraction in color-compensating prisms can be virtually eliminated by decentration of at least one lens used to focus the recombined image on the reticle. If the decentered lens is rotated with the compensation prism as a unit, deviation will not occur in any position of the color-compensating prism as it is rotated. If the lens is a strong lens, less decentration is necessary to correct a given amount of deviation than if the decentered lens is a weak lens. If a plurality of lenses are used to focus the image on the reticle, then one or more of the plurality may be decentered. It is usually desirable to have a color-compensated lens used to correct deviation, but this is not always necessary. Those skilled in the art can easily determine the amount of decentration required to correct for deviation. For purposes of correcting compensating prism deviation, the most desirable lens to decenter is one which is remote from the focal plane, i.e. the reticle, in order to have optimum potential for correction.

Since Abbe refractometers generally attempt to pass collimated light through the color-compensation prism, the lenses used to focus on the reticle are usually located between the color-compensating prism and the reticle.

FIG. 1 illustrates the principal components of an Abbe refractometer; and

FIG. 2 is a side view, partly in section, of one embodiment of the present invention.

DETAILED DESCRIPTION OF THE PREFERRED EMBODIMENT

Referring to FIG. 1, light from illumination source 1 is directed through primary prism 2 having a test sample (not shown) therein to moveable mirror 3. Light reflected from the mirror passes through color-compensating prism 4 and is focused by telescope lens 5 on reticle 6 which is observed through eyepiece 7. The detailed specification of such components and the parameters within which they must be manufactured are well known to those skilled in the art.

FIG. 2 illustrates preferred color-compensating prism 20 and telescope lens system 21 for imaging the light at reticle plane 22. The critical angles of prism 20 having components 30, 31 and 32 are identified as $\angle_1$ to $\angle_4$, respectively. The following Table provides exemplary values of compensating prism 20 as well as lens system 21 with all radii, $R_1$ to $R_9$; thicknesses, $T_1$ to $T_3$; and spacings, $S_1$ to $S_3$ being in millimeters. A minus sign (−) indicates a radius having a vertex on the reticle side of the surface. Angles are in degrees, while dispersion values (Abbe numbers) and indices of refraction are absolute values.

TABLE

| Optical Component | Radius (R) | Thickness (T) | Spacing (S) | Index of Refraction (ND) | Abbe No. ($\nu$) | Angle ($\angle$) |
|---|---|---|---|---|---|---|
| 30 | $R_1 = \infty$ | | | $ND_1 = 1.62096$ | $\nu_1 = 35.9$ | |
| | | | | | | $\angle_1 = 71.0°$ |
| | $R_2 = \infty$ | | | | | $\angle_2 = 19.0°$ |
| 31 | | | | $ND_2 = 1.62041$ | $\nu_2 = 60.33$ | |
| | | | | | | $\angle_3 = 19.0°$ |

Table -continued

| Optical Component | Radius (R) | Thickness (T) | Spacing (S) | Index of Refraction (ND) | Abbe No. (ν) | Angle (∠) |
|---|---|---|---|---|---|---|
| 32 | $R_3 = \infty$ | | | $ND_3 = 1.62096$ | $\nu_3 = 35.9$ | |
| | $R_4 = \infty$ | | | | | $\angle_4 = 71.0°$ |
| | | | $S_1 = 1.0$ | | | |
| 41 | $R_5 = -20.23$ | $T_1 = 3.0$ | | $ND_4 = 1.51680$ | $\nu_4 = 64.17$ | |
| | $R_6 = 14.816$ | | | | | |
| 427 | | $T_2 = 3.0$ | $ND_5 = 1.648131$ | | $\nu_5 = 33.84$ | |
| | $R_7 = 39.051$ | | | | | |
| | | | $S_2 = 11.6$ | | | |
| | $R_8 = 25.713$ | | | | | |
| 43 | | $T_3 = 2.1$ | | $ND_6 = 1.51680$ | $\nu_6 = 64.17$ | |
| | $R_9 = -25.713$ | | | | | |
| | | | $S_3 = 46.33$ | | | |

Doublet 40 of lens system 21 is color corrected and has a biconvex singlet 41 cemented to a concavo-convex singlet 42. A deviation of 1 mm at reticle plane 22 caused by angular error in prism 20 or mismatch of the index of refraction between components 30, 31 and 32 requires decentration of doublet 40 about 0.5 mm in direction opposite to the direction of decentration at reticle 22.

The optical system is carried by hollow support 100 which has cylindrical sidewall 101 adapted to be inserted into an eye tube (not shown) of an Abbe refractometer. Mount 102 is a hollow body with machined sidewalls 103 being complementary to inner surface 104 of support 100. Machined sidewalls 103 and inner surface 104 act as a bearing to permit rotation of the optical system to adjust color compensation. A plurality of adjustment screws 105 are used to align prism 20 at one end of mount 102. The other end of mount 102 has flange 106 which rests against a complementary recess 107 in support 100. At least three positioning screws 108 (two shown) are used to locate holder 109 for lens system 21. Complementary inner flange 110 of mount 102 and outer flange 111 on holder 109 maintain parallelinity between the axis of lens system 21 and the axis of the refractometer optical system. A V-shaped circumferential groove 112 is located on holder 109 so that the beveled ends 113 of positioning screws 108 contact the face of v-shaped groove 112 distal to outer flange 111. This arrangement assures parallelinity between the axes of the refractometer system and lens system 21 is maintained without extreme care to maintain axial uniformity during manufacture of all screws 108 and beveled ends 113. Lens 43 is cemented in externally threaded ring 114 which cooperates with internal threads of holder 109 for focusing light at reticle plane 22.

To practice adjustment according to the present invention, a standard wavelength (sodium) of light is passed through the unit shown in FIG. 2, while mount 102 is rotated. When maximum deflection from an axial reference is obtained, adjustment of screws 108 is made to decenter holder 109 in a direction opposite that of the original deflection until the deflection is cancelled. It may be necessary to repeat this procedure several times in order to obtain accurate positioning of lens system 21 to offset the errors of prism 20.

What is claimed is:

1. A method of reducing undesirable deviation caused by imperfections in a color-compensating prism of an Abbe refractometer having a reticle which comprises decentering a lens, located between the prism and the reticle, in a direction and by an amount effective to substantially cancel the undesirable deviation.

2. In an Abbe refractometer having a primary prism, a rotatable color-compensating prism for recombining light dispersed by the primary prism, and a lens for focusing recombined light on a reticle, the color-compensating prism having at least one imperfection causing deviation of the recombined light in a first direction from a reference position, the improvement comprising an axially-rotatable support means to position and rotate both said prism and said lens as a unit and said support means including adjustment means for moving said lens in a second direction opposite to said first direction whereby deviation caused by the color-compensating prism is substantially cancelled.

3. The improvement of claim 2 wherein said lens includes a plurality of lens element moveable as an assembly.

4. The improvement of claim 2 wherein said adjustment means includes four screws for orthogonally moving said lens.

* * * * *